(12) United States Patent
Gurley

(10) Patent No.: US 10,004,879 B2
(45) Date of Patent: Jun. 26, 2018

(54) CENTRAL VENOUS ACCESS SYSTEM

(71) Applicant: University of Kentucky Research Foundation, Lexington, KY (US)

(72) Inventor: John Gurley, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 255 days.

(21) Appl. No.: 15/131,257

(22) Filed: Apr. 18, 2016

(65) Prior Publication Data

US 2016/0263352 A1 Sep. 15, 2016

Related U.S. Application Data

(62) Division of application No. 12/958,702, filed on Dec. 2, 2010, now Pat. No. 9,314,595.

(60) Provisional application No. 61/363,436, filed on Jul. 12, 2010, provisional application No. 61/266,298, filed on Dec. 3, 2009.

(51) Int. Cl.
| | | |
|---|---|---|
| *A61M 25/00* | (2006.01) | |
| *A61M 25/06* | (2006.01) | |
| *A61M 25/01* | (2006.01) | |
| *A61B 6/12* | (2006.01) | |
| *A61B 17/34* | (2006.01) | |
| *A61M 29/00* | (2006.01) | |

(52) U.S. Cl.
CPC ............ *A61M 25/065* (2013.01); *A61B 6/12* (2013.01); *A61M 25/01* (2013.01); *A61M 25/0194* (2013.01); *A61B 17/3415* (2013.01); *A61B 17/3478* (2013.01); *A61M 29/00* (2013.01)

(58) Field of Classification Search
None
See application file for complete search history.

(56) References Cited

U.S. PATENT DOCUMENTS

| | | | |
|---|---|---|---|
| 4,559,039 A | 12/1985 | Ash et al. | 604/175 |
| 5,152,749 A | 10/1992 | Giesy et al. | 604/164.01 |
| 5,800,378 A | 9/1998 | Edwards et al. | 604/22 |
| 5,851,195 A | 12/1998 | Gill | 604/500 |
| 6,190,353 B1 | 2/2001 | Makower et al. | 604/95.01 |
| 6,217,527 B1 | 4/2001 | Selmon et al. | 600/585 |
| 6,475,226 B1 | 11/2002 | Belef et al. | 606/185 |
| 6,655,386 B1 | 12/2003 | Makower et al. | 128/898 |
| 6,662,036 B2 | 12/2003 | Cosman | 600/411 |
| 6,726,677 B1 | 4/2004 | Flaherty et al. | 604/528 |
| 7,059,330 B1 | 6/2006 | Makower et al. | 128/898 |
| 7,134,438 B2 | 11/2006 | Makower et al. | 128/898 |
| 7,179,220 B2 | 2/2007 | Kukuk | 600/101 |
| 7,635,353 B2 | 12/2009 | Gurusamy et al. | 604/170.03 |

(Continued)

FOREIGN PATENT DOCUMENTS

| | | |
|---|---|---|
| WO | WO 2006/105244 | 10/2006 |
| WO | WO 2009/100129 | 8/2009 |
| WO | WO 2011/068540 | 6/2011 |

OTHER PUBLICATIONS

International Search Report and Written Opinion issued in PCT/US2010/003078, dated Feb. 2, 2011.

(Continued)

*Primary Examiner* — Aarti B Berdichevsky
(74) *Attorney, Agent, or Firm* — Norton Rose Fulbright US LLP

(57) ABSTRACT

A catheter system and method of use for re-establishing venous access near an occluded vessel.

13 Claims, 16 Drawing Sheets

(56) References Cited

U.S. PATENT DOCUMENTS

| | | | |
|---|---|---|---|
| 7,678,081 B2 | 3/2010 | Whiting et al. | 604/164.13 |
| 8,029,470 B2 | 10/2011 | Whiting et al. | 604/164.01 |
| 8,337,518 B2 | 12/2012 | Nance et al. | 606/194 |
| 8,357,193 B2 | 1/2013 | Phan et al. | 623/1.12 |
| 8,500,768 B2 | 8/2013 | Cohen | 606/167 |
| 8,568,435 B2 | 10/2013 | Pillai et al. | 606/185 |
| 8,771,287 B2 | 7/2014 | Wynberg | 606/108 |
| 8,795,310 B2 | 8/2014 | Fung et al. | 606/185 |
| 2001/0016752 A1 | 8/2001 | Berg et al. | 606/180 |
| 2002/0022857 A1 | 2/2002 | Goldsteen et al. | 606/185 |
| 2003/0191449 A1 | 10/2003 | Nash et al. | 604/523 |
| 2003/0220698 A1 | 11/2003 | Mears et al. | 623/22.4 |
| 2004/0165966 A1 | 8/2004 | Aukzemas et al. | 411/353 |
| 2004/0181150 A1 | 9/2004 | Evans et al. | 600/433 |
| 2004/0199177 A1 | 10/2004 | Kim | 606/108 |
| 2005/0015048 A1* | 1/2005 | Chiu | A61M 25/10 604/101.04 |
| 2005/0021002 A1 | 1/2005 | Deckman et al. | 604/527 |
| 2005/0125002 A1 | 6/2005 | Baran et al. | 606/108 |
| 2005/0209579 A1 | 9/2005 | Yacoubian et al. | 604/500 |
| 2005/0288695 A1 | 12/2005 | Jenson et al. | 606/159 |
| 2006/0106288 A1 | 5/2006 | Roth et al. | 600/204 |
| 2007/0135803 A1 | 6/2007 | Belson | 606/1 |
| 2007/0166345 A1 | 7/2007 | Pavcnik et al. | 424/423 |
| 2007/0203517 A1 | 8/2007 | Williams et al. | 606/191 |
| 2008/0230070 A1 | 9/2008 | Gregorian | 128/207.14 |
| 2009/0005755 A1 | 1/2009 | Keith et al. | 604/509 |
| 2009/0240122 A1 | 9/2009 | Avitsian | 600/309 |
| 2009/0281379 A1 | 11/2009 | Binmoeller et al. | 600/106 |
| 2010/0056862 A1 | 3/2010 | Bakos | 600/106 |
| 2010/0249491 A1 | 9/2010 | Farnan et al. | 600/16 |
| 2012/0136247 A1 | 5/2012 | Pillai | 600/433 |
| 2012/0136320 A1 | 5/2012 | Pillai et al. | 604/272 |
| 2012/0136366 A1 | 5/2012 | Pillai | 606/108 |
| 2012/0239069 A1 | 9/2012 | Benscoter et al. | 606/185 |
| 2013/0197621 A1 | 8/2013 | Ryan et al. | 623/1.11 |
| 2014/0142418 A1 | 5/2014 | Gurley et al. | 600/424 |

OTHER PUBLICATIONS

Office Action issued in U.S. Appl. No. 12/958,702, dated Dec. 28, 2012.

International Search Report and Written Opinion issued in PCT/US2013/024738, dated Apr. 30, 2013.

International Preliminary Report on Patentability issued in PCT/US2013/024738, dated Feb. 18, 2014.

Office Action issued in Chinese Patent Application No. 2013800090393, dated Jun. 20, 2016. (English Translation Provided).

Office Action issued in U.S. Appl. No. 13/680,327, dated Jan. 29, 2014.

Office Action issued in U.S. Appl. No. 13/680,327, dated Nov. 7, 2014.

Office Action issued in U.S. Appl. No. 13/680,327, dated May 29, 2014.

* cited by examiner

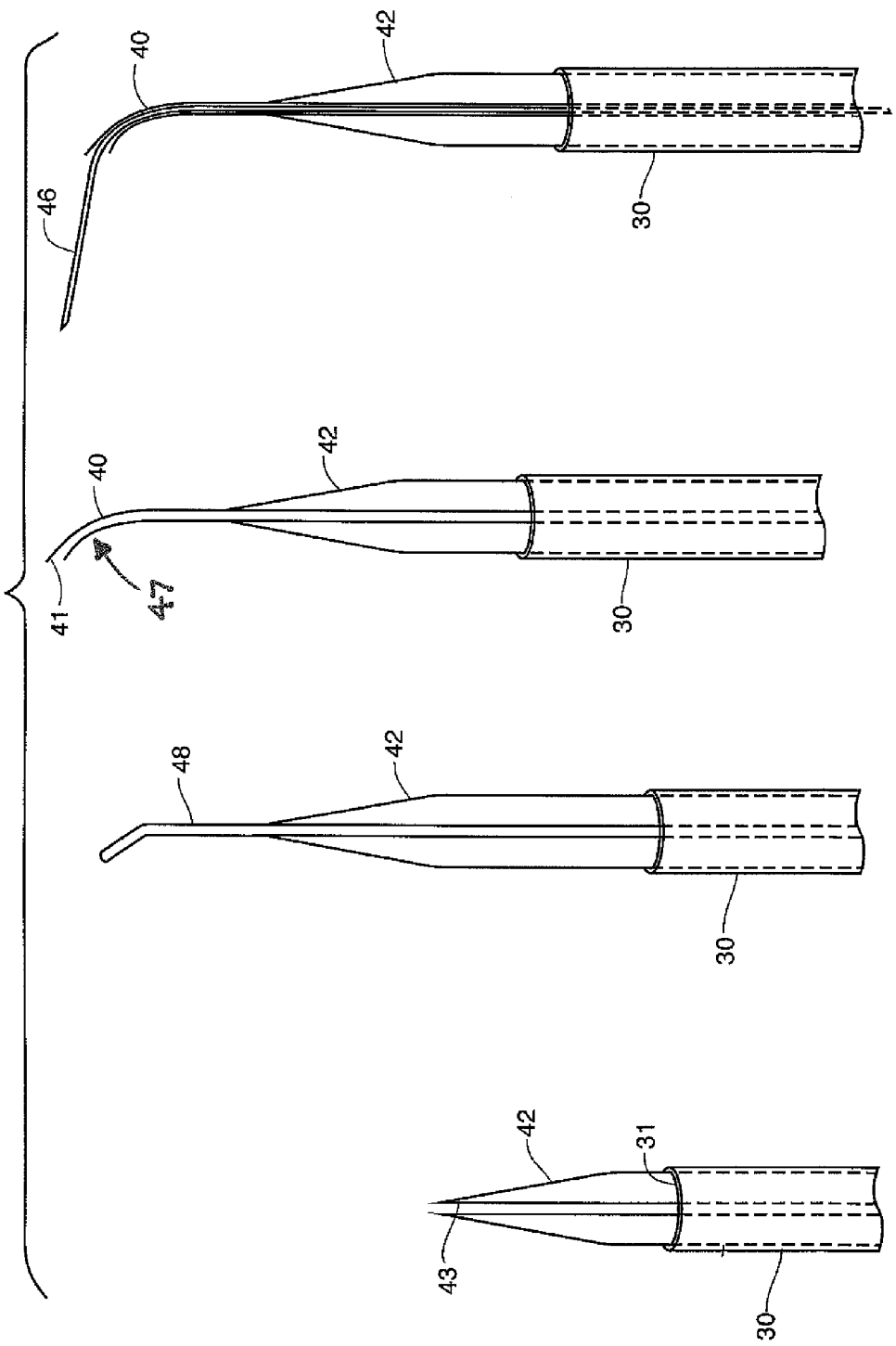

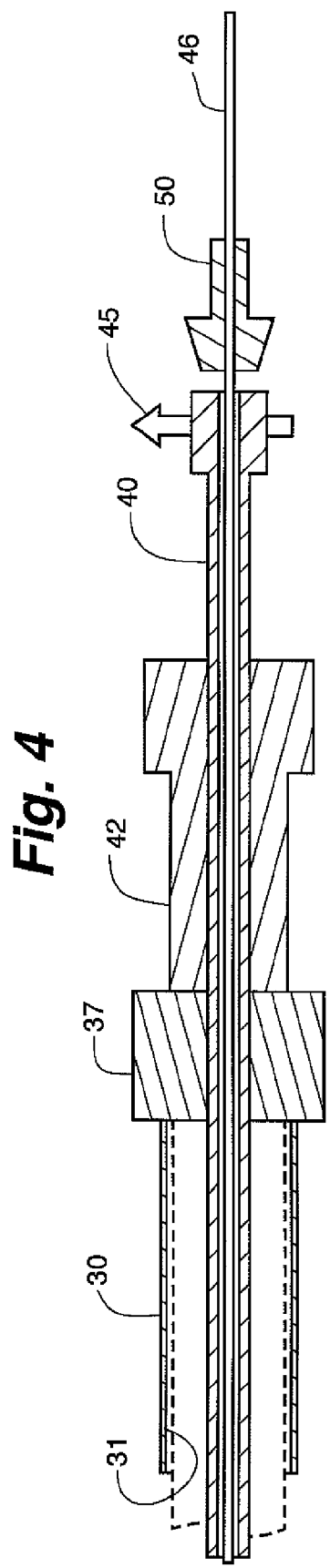

CENTRAL VENOUS ACCESS SYSTEM

CROSS REFERENCE TO RELATED CASES

The present application is a division of U.S. patent application Ser. No. 12/958,702 filed Dec. 2, 2010, which claims the benefit of both U.S. Provisional Application 61/363,436 entitled "CENTRAL VENOUS ACCESS METHOD, SYSTEM and DEVICES" filed 12 Jul. 2010; and U.S. Provisional Application 61/266,298 entitled "INSIDE/OUT CENTRAL VENOUS ACCESS and APPARATUS" filed 3 Dec. 2009. The entire contents of each of the above-referenced disclosures are specifically incorporated herein by reference without disclaimer.

BACKGROUND OF THE INVENTION

Central venous access (CVA) is one of the most commonly performed procedures in medicine. CVA is vital to many patients with acute and chronic illness. Hemodialysis and cardiac pacing are examples of life-sustaining therapies that would not be possible without central venous access.

CVA is typically obtained by using a large gauge needle to directly puncture first the skin and then one of the four large upper body veins, for example, the right or left internal jugular vein, or the right or left subclavian vein. After puncture, a guidewire is introduced through the needle and advanced into the central circulation. The channel is then dilated and a catheter or other medical device is advanced into the superior vena cava (SVC) or right atrium (RA).

Although central venous access is usually a straightforward procedure, there can be both short term and long term complications. Immediate risks include bleeding due to inadvertent puncture of carotid or subclavian arteries, and pneumothorax due to unintended puncture of a lung. These complications occur because central veins lie deep beneath the skin and are therefore not visible to the operator. As a result, there is often uncertainty about the location, depth and entry angle of the puncture needle, even when ultrasound guidance is used. The long-term risks of central access include venous occlusion, which can occur within days and is a common problem in patients requiring repeated access or semi-permanent access. Chronic venous occlusions occur when thrombus forms around a catheter or pacing lead, and then organizes into dense fibrous tissue that permanently obliterates the vessel lumen.

When confronted with occlusion of a central vein, physicians usually utilize one of the remaining veins in the upper body. The process can continue until all four central veins have been obliterated. However, once all four upper body central veins are lost the patient can have a life threatening access crisis.

SUMMARY OF THE INVENTION

The method is carried out by intravascular navigation of a catheter system that includes specialized devices serving multiple functions. An exit point target site is identified for example near the clavicle on the exterior of the patient's body. The specialized set of intravascular devices in the catheter system are navigated from a remote entry point for example, in the groin to a position proximate the desired exit point target site. A very sharp needle wire is pushed through the catheter system and is directed by the catheter system in a defined and desired direction. Passage of this needle wire forms an extra-vascular tissue track from the vessel to the skin near the exit point target site.

With the needle wire pushed through the skin and exteriorized, companion devices are pushed and/or pulled through the tissue track enlarging it and preparing it for the placement of an access port or pacing lead or the like. The combination of pushing and pulling motions enabled by the catheter system allows for the safe and quick access or re-acquisition of a lost access site to the central venous system. In many instances the ability to work close to thrombus and near occlusions with great precision allows the recovery or salvage of an otherwise lost venous access location, which is a significant benefit to the patient.

DESCRIPTION OF THE DRAWINGS

In the several figures of the drawings, identical reference numerals are used to identify identical or equivalent structure wherein:

FIG. 3 is a schematic representation of the distal ends of elements of the catheter system;

FIG. 4 is a schematic diagram showing an assembly of the proximal ends of the catheter system;

DETAILED DESCRIPTION OF THE INVENTION

One of the most clinically significant uses of the devices and methods of this invention pertains to right-sided supraclavicular access because it combines the preferred location for long-term catheters, the most common site of chronic venous occlusions, and the most straightforward application of the invention. Therefore this procedure has been selected as an illustrative but not limiting example of the techniques and suitable hardware implementations of the catheter system invention. The invention is illustrated in the context of a patient having an occluded right internal jugular vein which is recovered by use of the method and catheter system to place a new access point near the one lost to the occlusion. In contrast to the conventional practice that would sacrifice companion vessels, the illustration achieves re-entry very near a lost CVA location.

Figure 1:
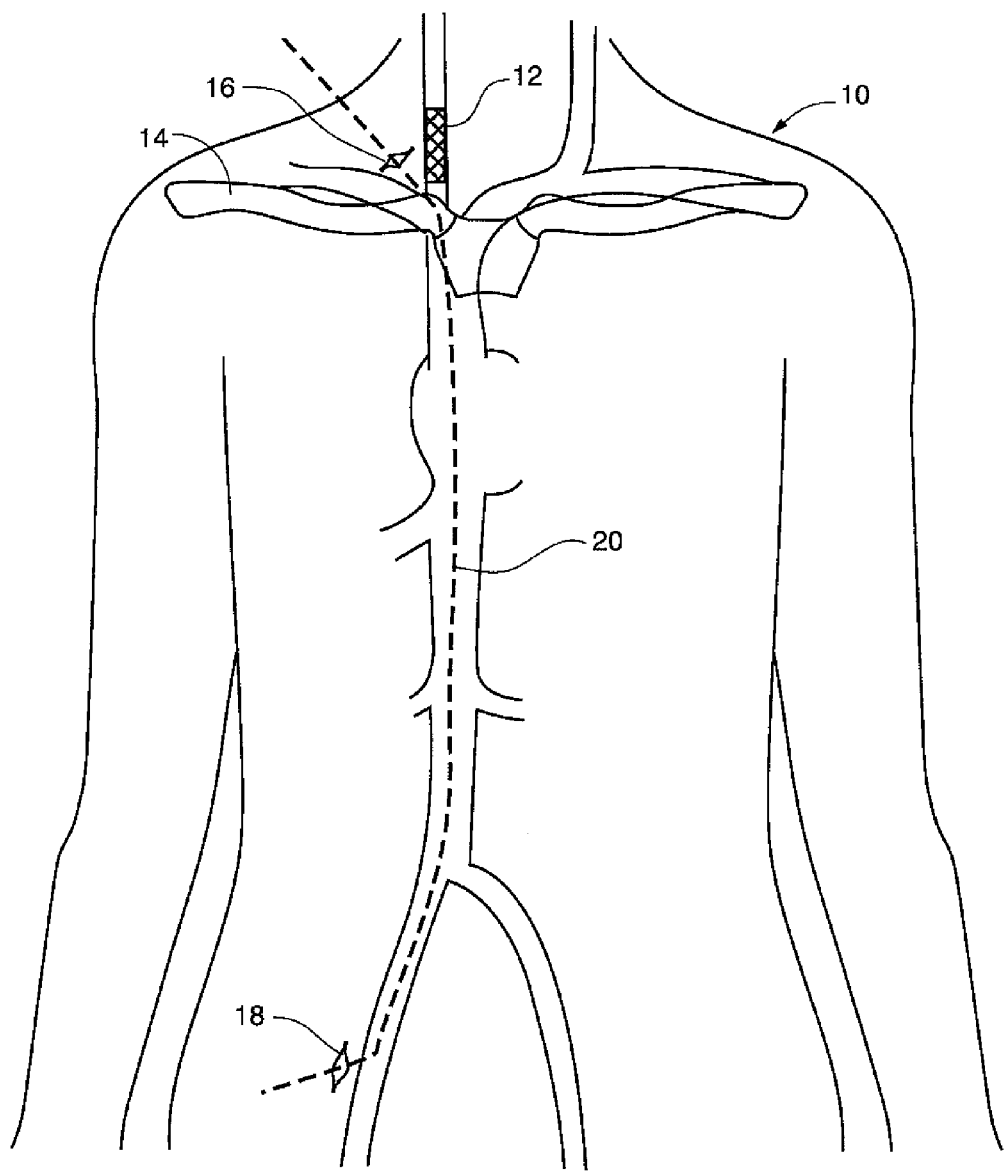
FIG. 1 is a schematic diagram showing a portion of the venous system of a patient.
Figure 2A:
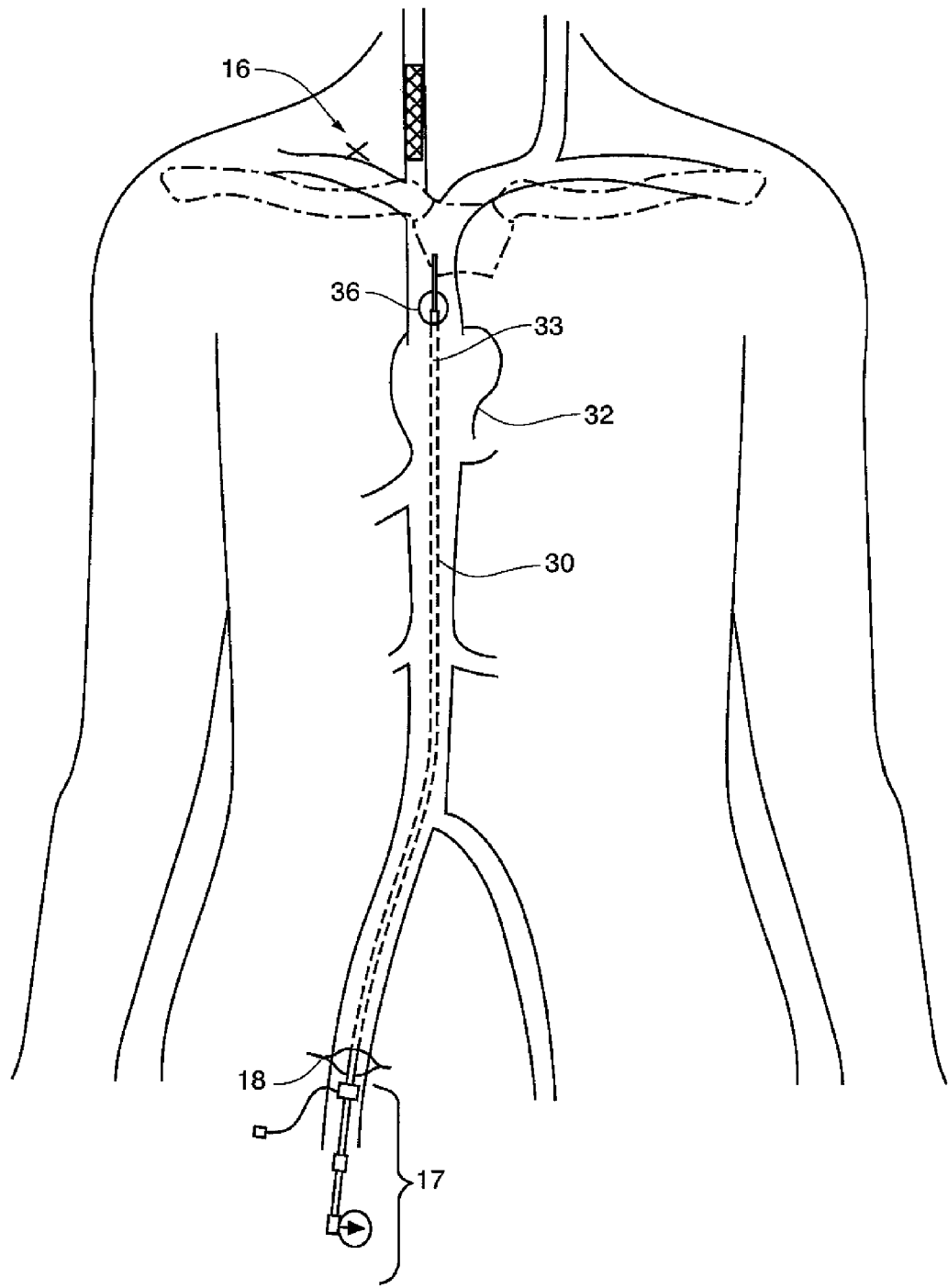
FIG. 2A is a plan view schematic diagram showing the use of a catheter system to access the central venous system.
Figure 2B:
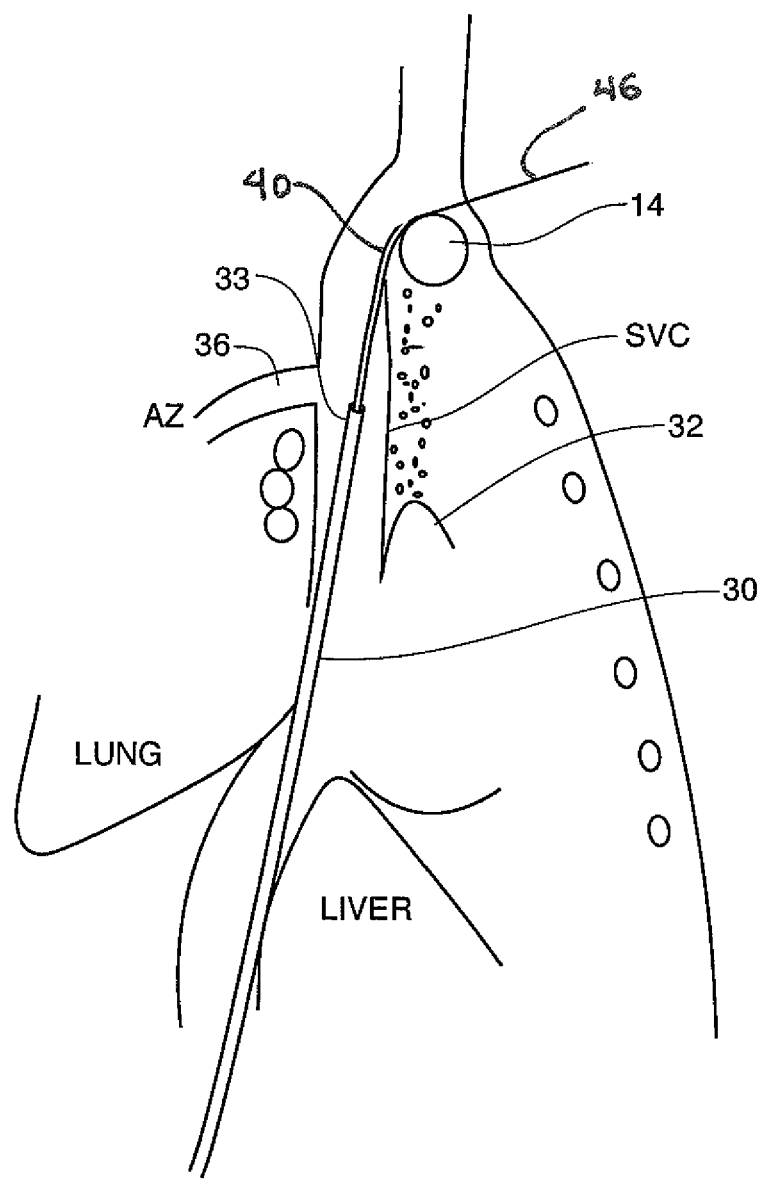
FIG. 2B is a cross-sectional schematic diagram showing a side view of the system of FIG. 2A.

FIG. 1 shows the context of the invention and presents the interventional path with respect to certain anatomic reference points. FIG. 2A and FIG. 2B should be considered together and together they show the placement of the rigid guide catheter work station with regard to preferred anatomic reference points. FIG. 2A also shows the proximal end portions of elements of the catheter system extending out of the patient's body. FIG. 3 shows the distal end portions of catheter system elements. FIG. 4 shows the proximal ends of catheter systems elements. The intermediate portions of the catheter elements are not shown for clarity but they should be understood to continue from the distal to the proximal ends and have overall lengths suitable for the size of the patient, and will be on the order of 200 cm overall or more for an adult case. FIG. 5 through FIG. 15 depicts steps in an illustrative fashion of a method of using the catheter system.

FIG. 1 shows a patient 10 with an occluded right internal jugular vein indicated by the cross-hatched occlusion in the vessel at reference numeral 12. The method and devices of the invention are used to re-acquire access to the central venous system through an exit point target location 16 near and slightly above the collar bone or clavicle 14. Beginning at a remote entry point 18 near a large femoral vein in the groin of the patient, the interventional path is seen as a dashed line at reference numeral 20. In practice the surgeon will use conventional techniques to enter the femoral vein then introduce the inventive catheter system and use it to follow the interventional path 20 forming an exit through the skin of the body near the clavicle at the exit point 16 in this illustrative description. Once an appropriate tissue track is established between the exit location 16 and the central venous system the tissue track will be prepared for the delivery of a conventional CVA access port or other device concluding the access procedure.

FIG. 2A is a schematic illustration depicting the placement of the rigid guide catheter work station 30 placed along the interventional path with the distal tip 33 of the work station located above the right atrium 32 at about the level of the ostium of the azygos vein seen at 36. The exit target location is shown at 16 and the remote entry point is shown at 18. Proximal portions of the catheter system extend out of the groin area and they are collectively labeled 17. The physician manipulates these proximal ends of elements of the catheter system rotating, retracting and advancing them to navigate through the vasculature, while observing the locations of the distal ends of the devices under fluoroscopy.

FIG. 2B is a schematic cross section of the patient with anatomic landmarks called out in the figure showing the placement of the rigid guide catheter work station 30, and is a side view of FIG. 2A. The figure shows successful deflection anteriorly of the rigid guide catheter work station 30 at the junction of the IVC and RA 32. This places the distal tip 33 of the workstation against the anterior wall of the SVC. This forces or biases the distal tip 33 against the wall of the vessel and also protects posterior structures from involvement with the catheter system. Once this placement is achieved the work station 30 remains relatively stationary during the rest of the procedure until it is ultimately removed from the body.

FIG. 3 shows the distal tips of various elements of the catheter system assembled in various configurations or combinations in several panels. The relatively long rigid guide catheter work station 30 can support various devices within its working lumen 31. It is expected that suitable performance can be achieved by manufacturing the rigid guide catheter 30 with conventional techniques well known in the art in a diameter of about 8F permitting the device to delivered through an 8F introducer. Both metal and braided structures are expected to be suitable.

In the figure the dilation stylet 42 is shown within the lumen 31 of the rigid guide catheter work station 30. The dilation stylet 42 is free to move within the lumen 31. Depending on the point in procedure, the central working lumen 43 of the dilation stylet 42 may carry and support either the canalization wire 48 or the needle wire directional guide 40. The needle wire directional guide 40 has a central lumen 41 adapted to receive the needle wire 46. The distal tip of the needle wire 46 is quite sharp and acts like a trocar to cut and divide tissue as it is pushed. The stiffness of the device and its sharpness must be selected so that it can be pushed through tissue. A sharpened nitinol. 014 wire has approximately the correct properties for the needle wire. Note as well that the distal tip of the needle wire directional guide 40 forms a gentle curve 47 to direct and deflect the needle wire 46 in a specific direction. It is expected that this portion of the device will be manufactured from a shape memory material such as nitinol, with the gentle curve 47 formed where the needle wire directional guide 40 emerges from the distal tip of the dilation stylet 42. The gentle curve will direct the needle wire through an angle near 90 degrees or so.

FIG. 4 shows the proximal ends of some of the components assembled into working configurations. In general, the rigid guide catheter work station 30 is placed at the correct location previously described and it remains largely stationary once positioned. An associated valve and flush port with Luer fittings is provided to introduce fluids to clear the devices and occasionally introduce contrast agent. The hemostasis valve and flush valve are shown schematically labeled 37 in the figure. Operation and configuration will be described in more detail in the steps of the method.

Figure 5:
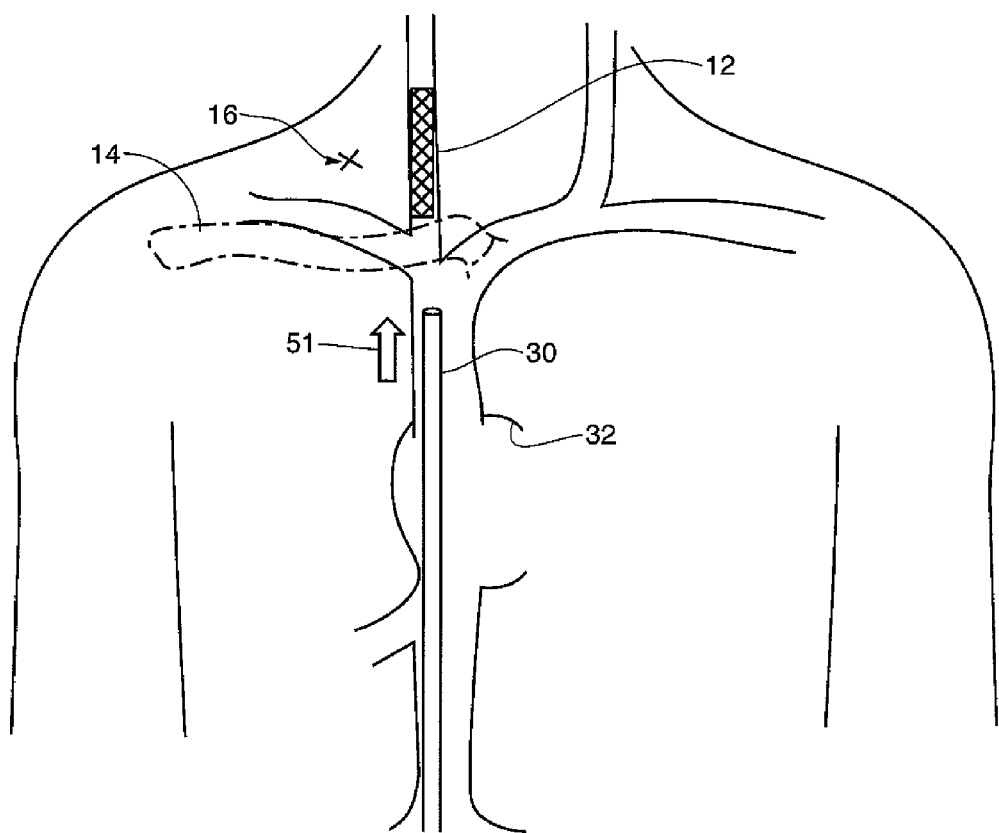
FIG. 5 is a schematic depiction of a step in the process and illustrates the function of an element of the catheter system.

FIG. 5 shows a step in the method. As a prelude to this step the entry and exit points on the skin of the patient will be identified and perhaps marked. Next the vascualture will have been accessed via a conventional Seldinger procedure. At his time the rigid guide catheter work station 30 is introduced over a wire into the venous circulation. The straightness of the vasculature and the straightness of the rigid guide catheter workstation 30 allow for navigation, indicated by arrow 51, of the distal end of the catheter workstation 30 to the preferred location in the figure above the right atrium RA 32, below the occlusion 12 and near the clavicle 14.

Figure 6:
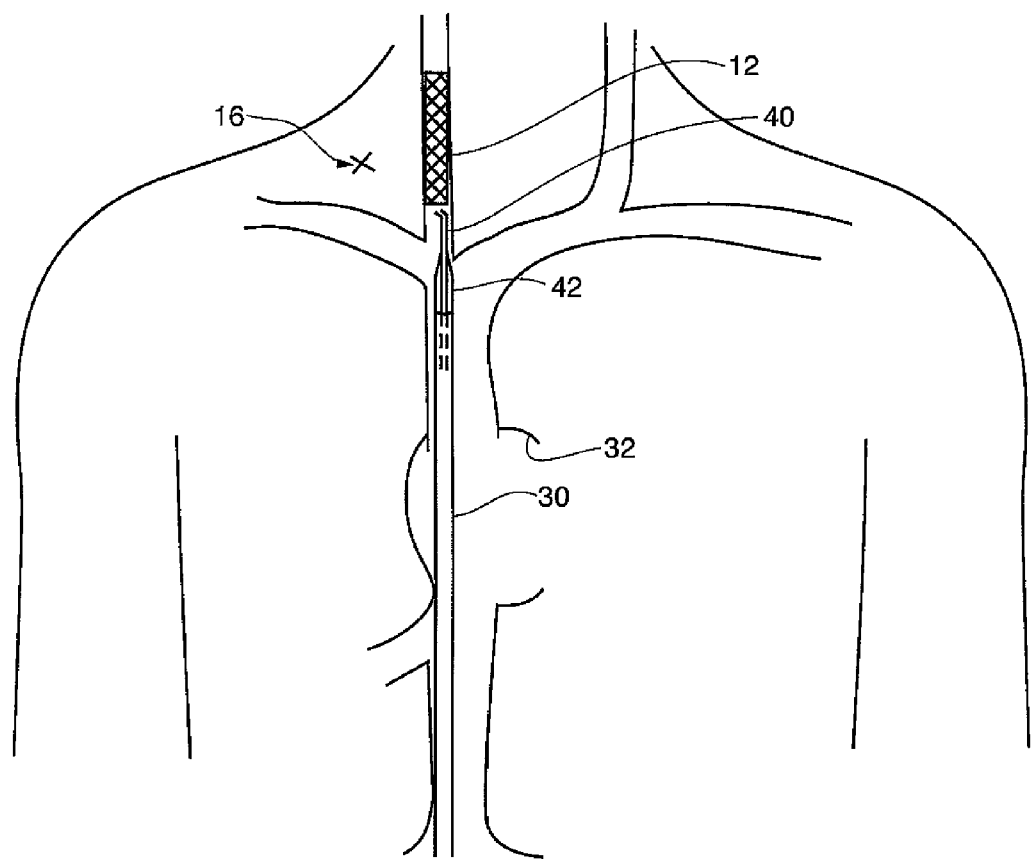
FIG. 6 is a schematic depiction of a step in the process and illustrates the function of an element of the catheter system.

FIG. 6 shows a step in the method. Next the dilation stylet 42 is advanced out of the rigid catheter work station with the needle wire directional guide 40 to about the occlusion 12 which is typically verified with a contrast injection. The physician manipulating the directional guide arm 45 aims the needle wire directional guide 40 so that the exit port lumen 41 points toward the exit location target site 16 identified on the skin of the patient. Although it is difficult to illustrate the placement of the rigid guide catheter work station 30 it is placed along the anterior wall of the SVC so that the needle wire guide 40 and dilation stylet 42 can be advanced safely toward the occlusion without interfering with other structures. At this point the needle wire directional guide port or lumen 41 is a short distance from the target exit point 16.

Figure 7:
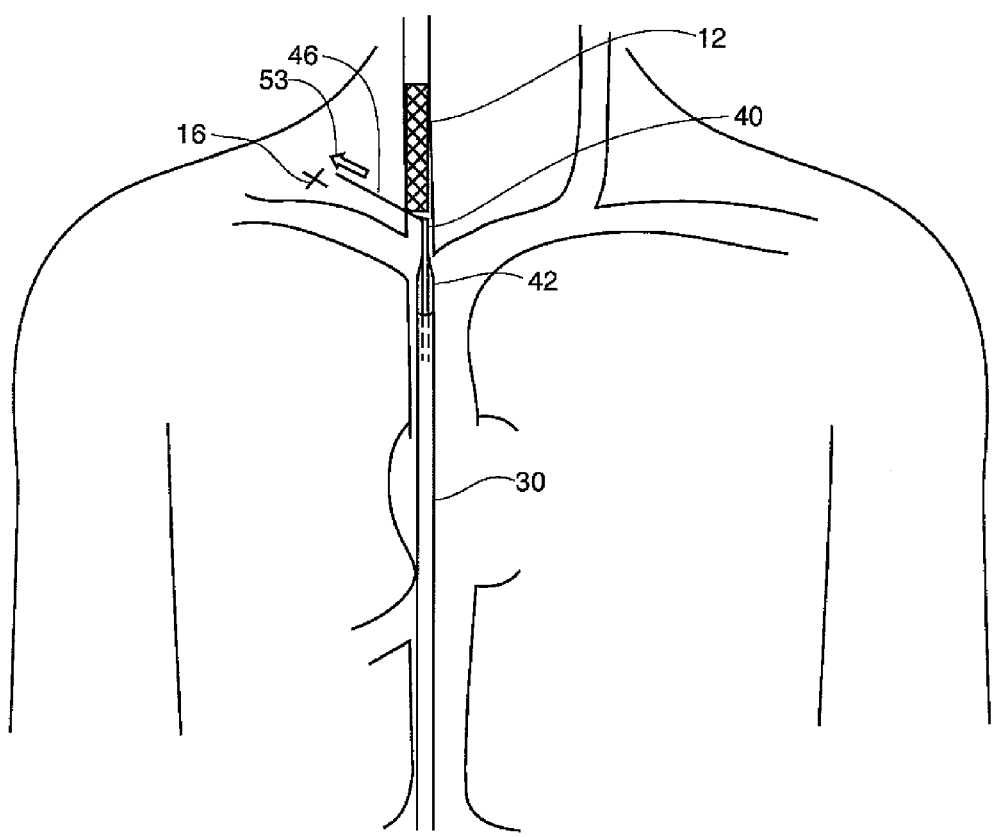
FIG. 7 is a schematic depiction of a step in the process and illustrates the function of an element of the catheter system.

FIG. 7 shows a step in the method. With aiming completed the physician can push the wire clamp 50 (FIG. 4) to advance the needle wire 46 out of the lumen 41 of the needle wire directional guide 40 and dissect a tissue path toward the clavicle as indicated by force and motion arrow 53 defining an extra vascular tissue track. The rigidity of the rigid catheter work station 30 and its placement allow the reaction forces from the needle wire 46 advancement to be taken up the rigid guide catheter work station and dilation stylet 42 and transferred to the body. The cross section of FIG. 2B also depicts this step with the needle wire 46 actually exteriorized in that figure.

Figure 8:
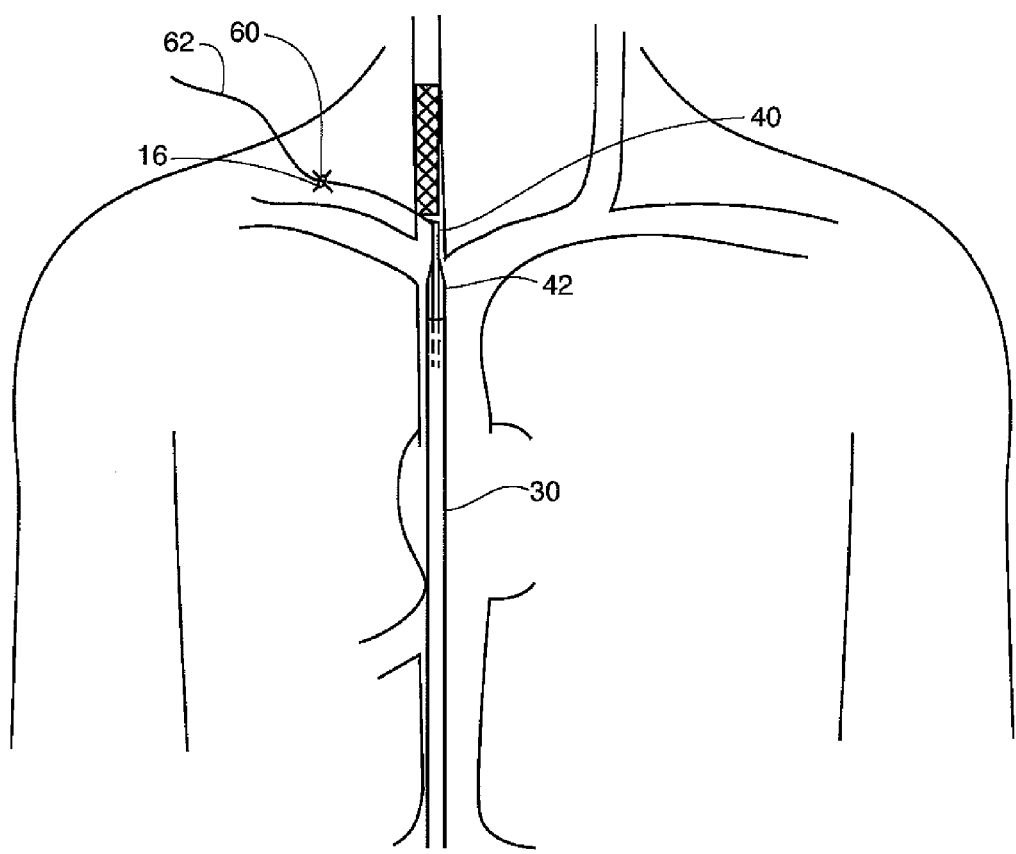
FIG. 8 is a schematic depiction of a step in the process and illustrates the function of an element of the catheter system.

FIG. 8 shows a step in the method. The physician continues to advance the needle wire 46 until it becomes exteriorized at the exit point 16. The small wound depicted at reference numeral 60 indicates the exit point. The needle wire 46 segment labeled 62 lies outside the body.

Figure 9:
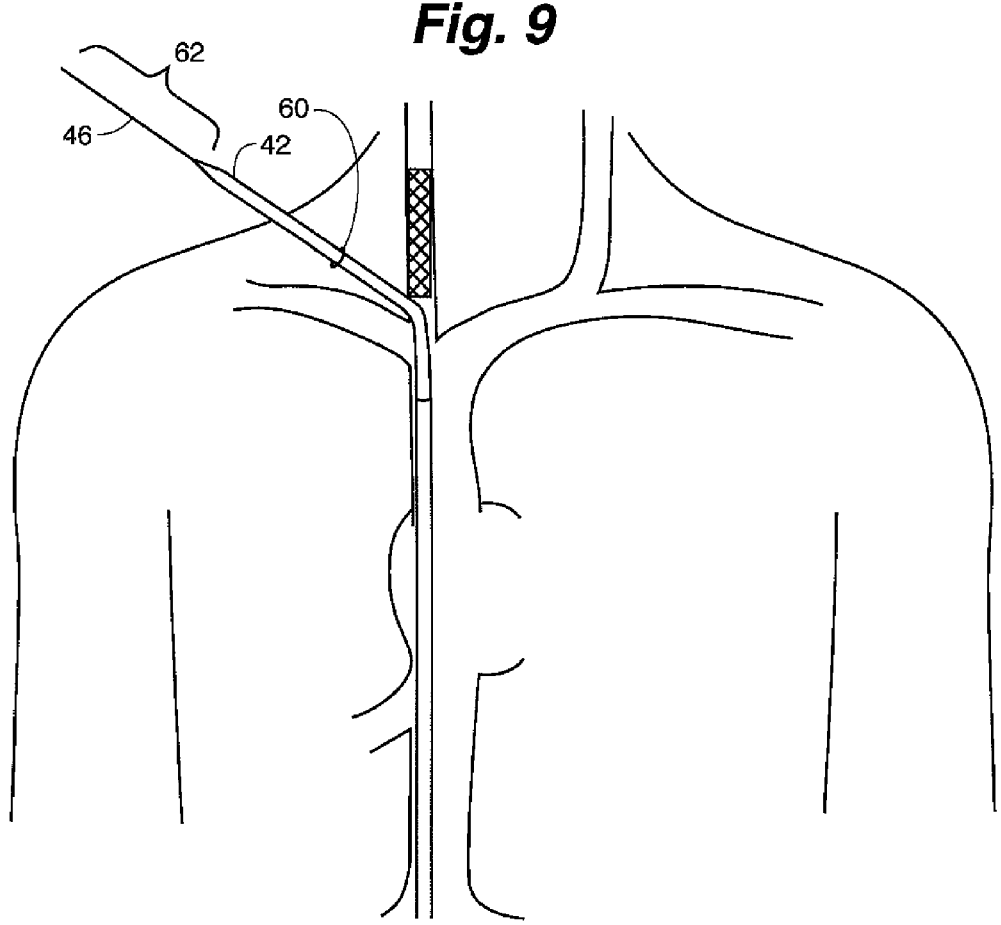
FIG. 9 is a schematic depiction of a step in the process and illustrates the function of an element of the catheter system.

FIG. 9 shows a step in the method. The physician will next clamp the needle wire 46 to the dilation stylet 42 with a wire clamp 50 or similar device at the proximal ends of the devices as depicted in FIG. 4. and apply traction to the exterior segment of the needle wire 62 pulling the dilation stylet 42 out of the body through the exit point enlarging the tissue track created by the passage of the needle wire 46.

Figure 10:
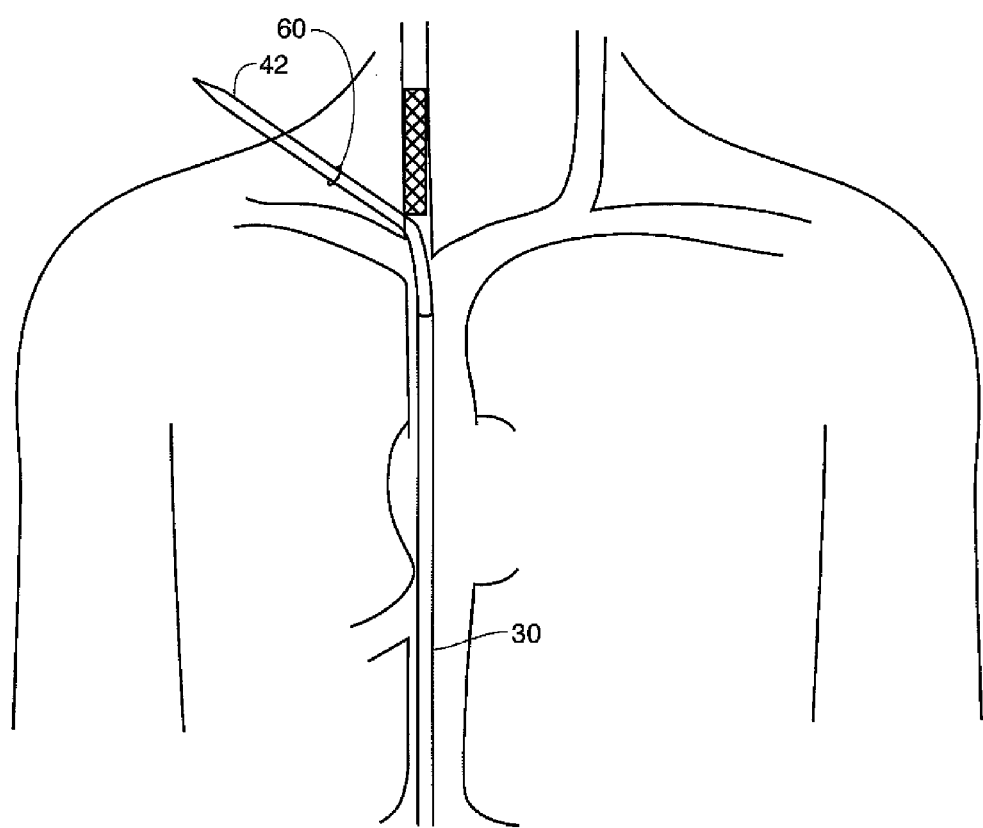
FIG. 10 is a schematic depiction of a step in the process and illustrates the function of an element of the catheter system.

FIG. 10 shows a step in the method. The physician may next remove the needle wire 46 and the needle wire directional guide 40 leaving the dilation stylet exteriorized and its central lumen 43 empty.

Figure 11:
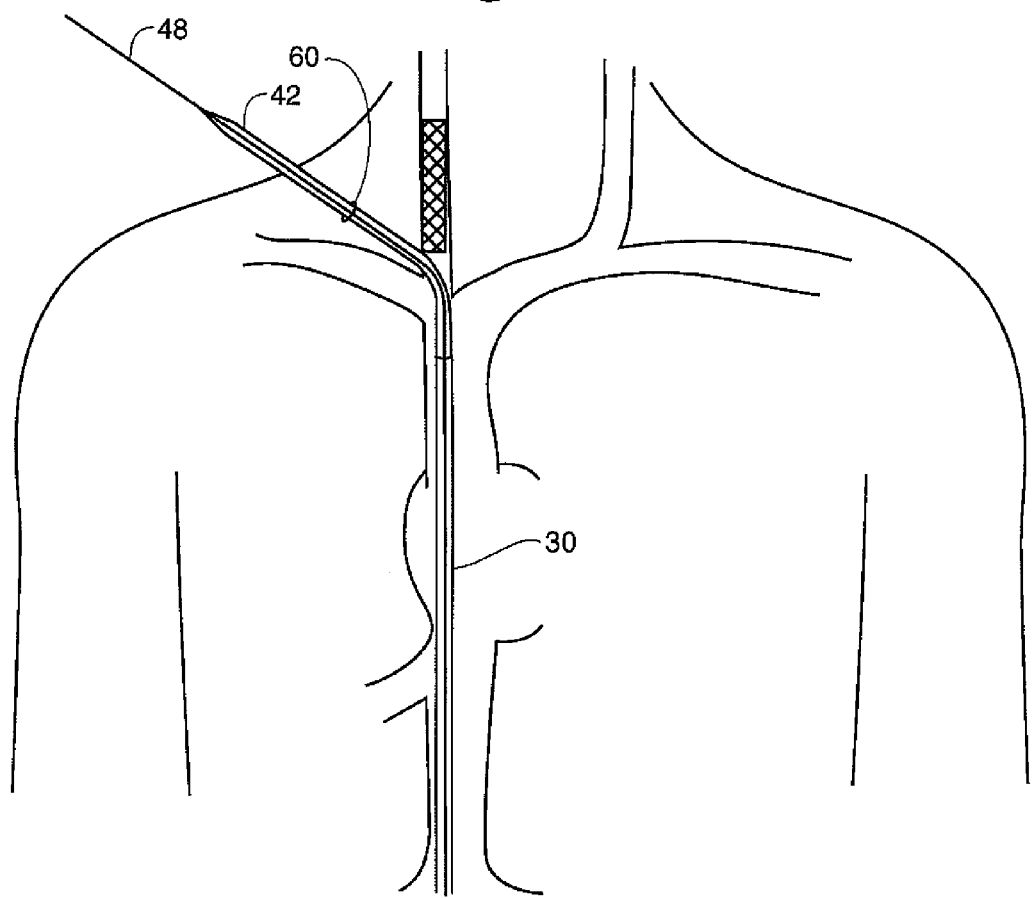
FIG. 11 is a schematic depiction of a step in the process and illustrates the function of an element of the catheter system.

FIG. 11 shows a step in the method. With the dilation stylet 42 exposed outside the patient the physician may then load or backload a larger gauge wire such as a canalization wire 48 or other guide wire product into the lumen of the dilation stylet. This larger diameter wire will support the next stages of the intervention. The wire size and type is driven mostly by the device that is to be implanted. In the illustrative process a CVA dialysis type port is to be implanted using a conventional introducer sheath 64.

Figure 12:
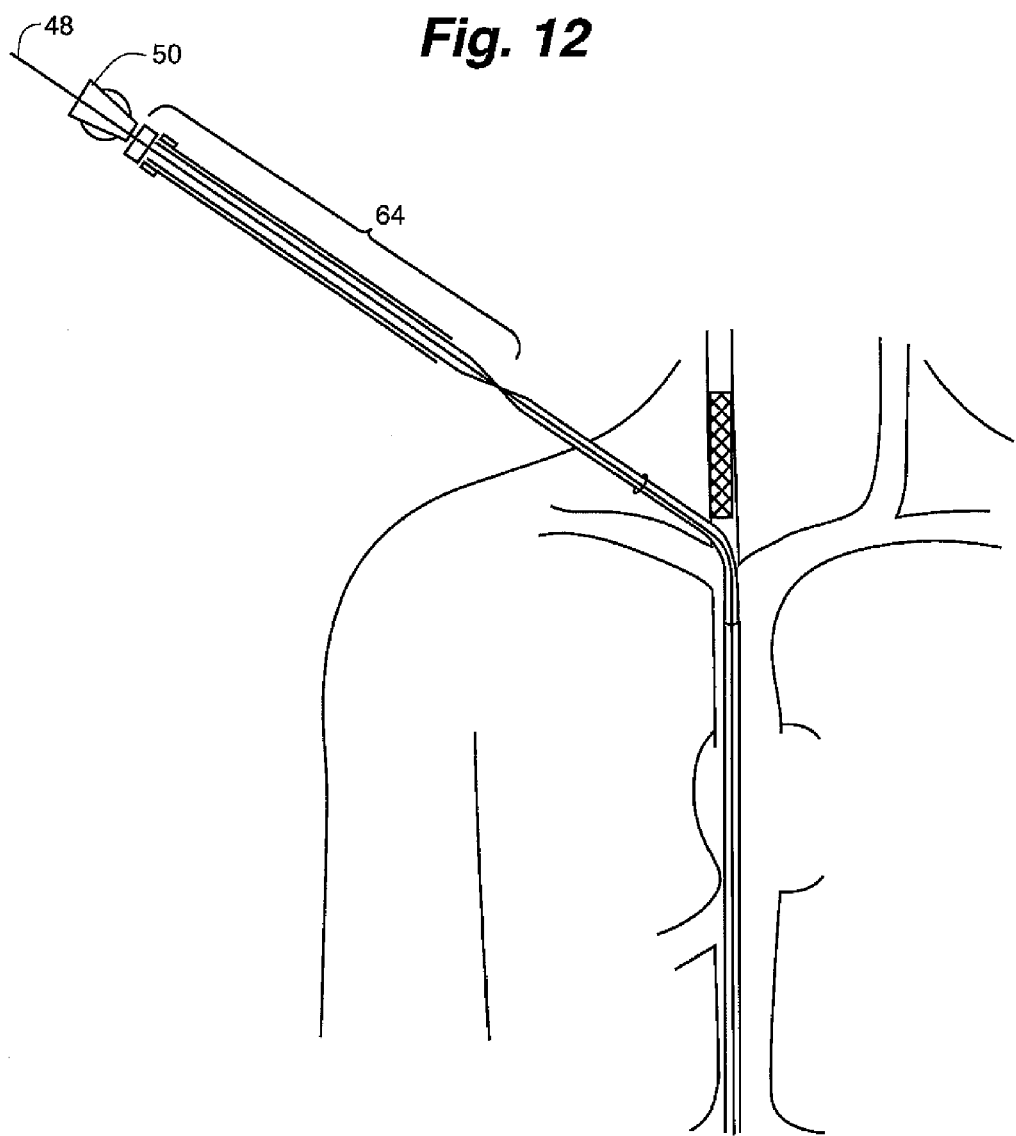
FIG. 12 is a schematic depiction of a step in the process and illustrates the function of an element of the catheter system.

FIG. 12 shows a step in the method. The physician may load the conventional introducer sheath 64 onto the canalization wire 48 and clamp them together with a wire clamp 50 or the like. The physician has a choice of pulling the introducer along the extra vascular tissue track by tugging on the proximal portions of the dilation stylet and canalization wire or pushing it along the tissue track from the distal end of the system or doing both sequentially or simultaneously.

Figure 13:
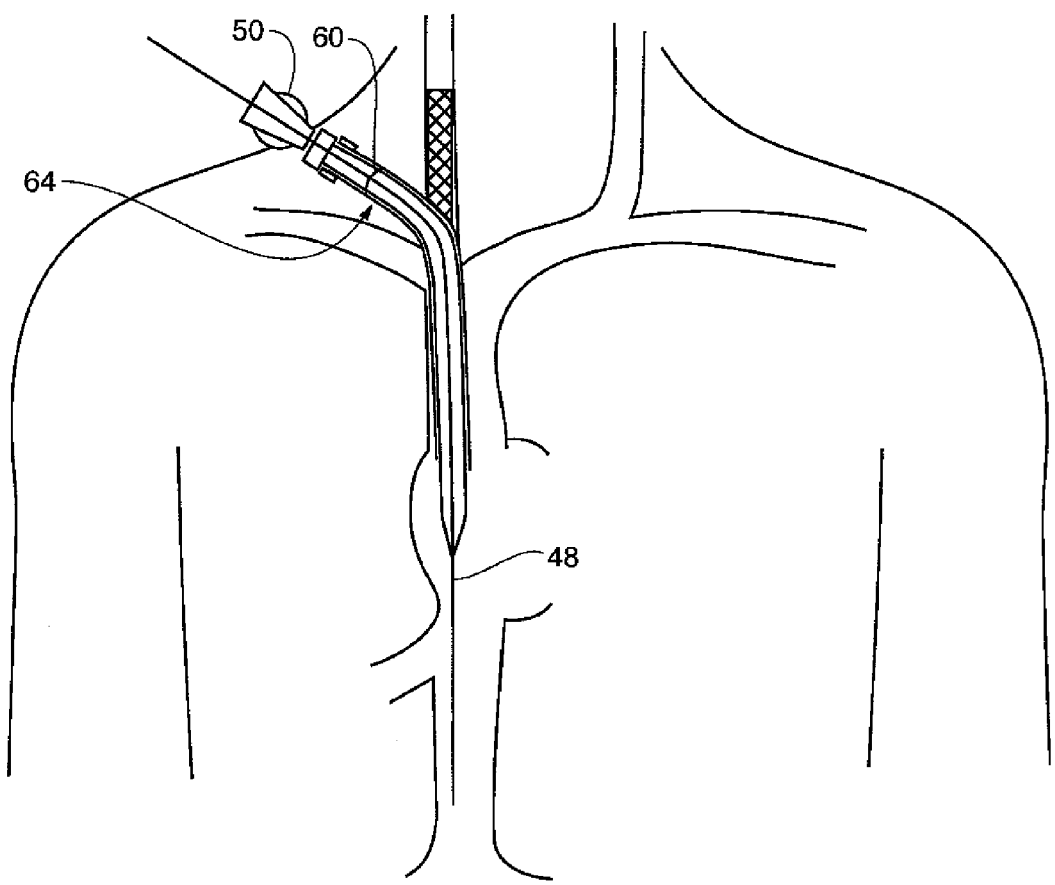
FIG. 13 is a schematic depiction of a step in the process and illustrates the function of an element of the catheter system.

FIG. 13 shows a step in the method. This figure shows the introducer sheath 64 placed into the central venous system just below the level of the occlusions thus salvaging the location. This figure shows the introducer 64 in place and the physician may remove the rigid guide catheter workstation and related devices from the femoral entry point. The physician may leave a guide wire in place depending on the course of the procedure.

Figure 14:
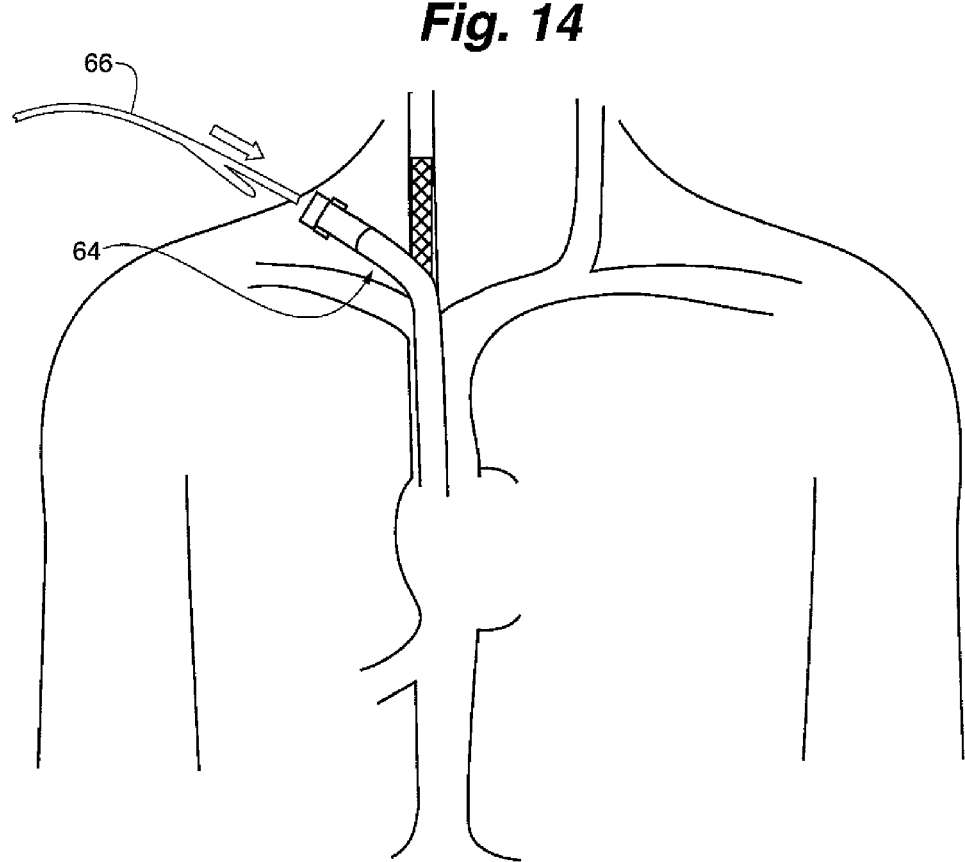
FIG. 14 is a schematic depiction of a step in the process and illustrates the function of an element of the catheter system.

FIG. 14 shows a step in the method. The physician may access the lumen of the convention al introducer 64 to permit the insertion of the dialysis port 66, though the lumen of the introducer. The precise sequence and hemostasis management will depend on the particularities of the port and the introducer and is not part of the invention apart from illustrating the utility of the procedure.

Figure 15:
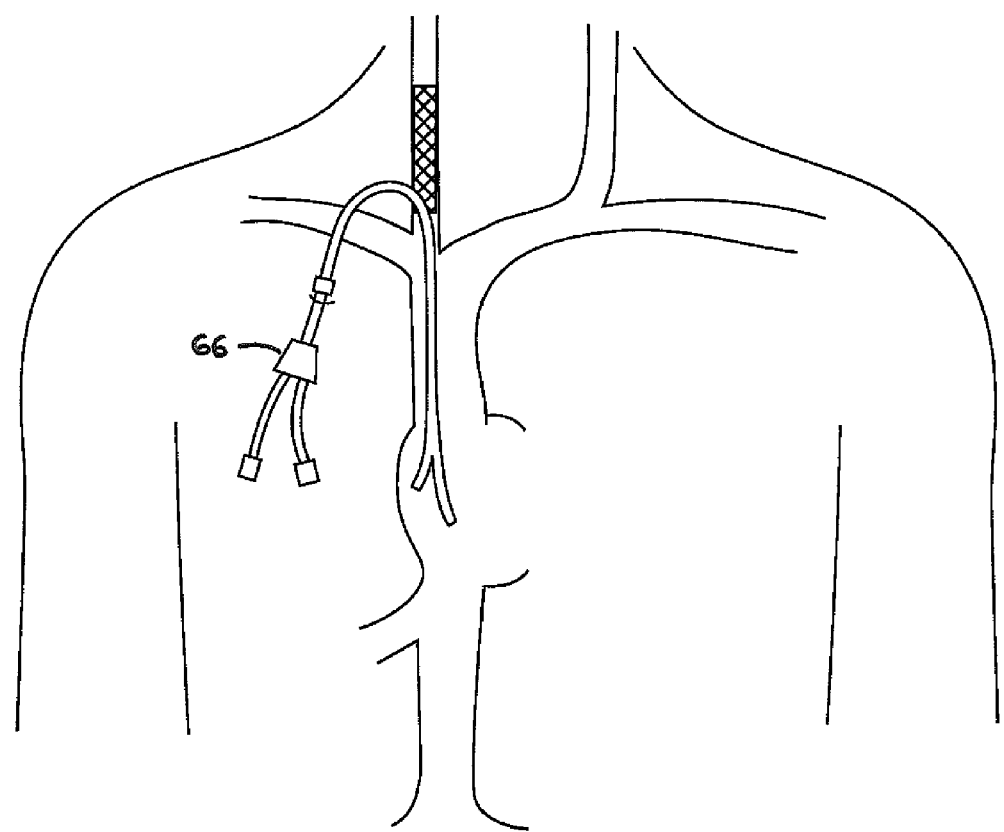
FIG. 15 is a schematic depiction of a step in the process and illustrates the function of an element of the catheter system.

FIG. 15 shows a dialysis port 66 placed in the patient via the catheter system and method. This port lies in a desirable location that would have been otherwise lost.

SUMMARY

The method and suite of devices that make up the catheter system can be used to acquire or re-acquire CVA allowing for the salvage or reuse of vessels and locations that are lost to conventional methods and devices. The method is dependent upon the use of particular devices having specific qualities. The rigid guide catheter work station must be stiff enough to resist reaction forces supplied by the needle wire as it dissects tissue and establishes the tissue track. The needle wire must be stiff enough to dissect tissue when pushed from its proximal end. It must be stiff enough to not wander off course and a very sharp trocar like tip aids in minimizing the force required for dissection. The needle wire directional guide must not whip or kink while it is being aimed under X-ray guidance.

It is also noted that there is much flexibility in the procedure and the system and apparatus used to carry out the method. Some variation in the method will reflect operator preference or the state or size of the patient. For this reason the descriptions herein are intended to be illustrative and not limiting. In a similar fashion the set of specialized medical devices illustrated for carrying out the invention can be supplemented or truncated and certain functions can be carried out with alternate devices. As a consequence the description of the favored hardware should be considered illustrative and not limiting.

What is claimed is:

1. A method for acquiring access to the central venous system of a patient at a target location near an occlusion of a jugular vein, comprising the steps of:
   introducing a guide catheter into a blood vessel at a location remote from said occlusion;
   advancing a needle wire having a sharp end transvascularly through the guide catheter until its sharp end is adjacent the occlusion;
   rotationally adjusting said needle wire until its sharp end is aimed toward the desired skin exit location;
   advancing the needle wire to puncture the blood vessel from the inside out at a vascular exit site adjacent the occlusion, thereby establishing a tissue track;
   further advancing the needle wire along said tissue track thereby extending said tissue track to puncture the skin from the inside out near said vascular exit site.

2. The method of claim 1 further including the steps of:
enlarging said tissue track by sequential dilation.

3. The method of claim 2 wherein said enlarging step includes;
   clamping said needle wire and said dilation stylet together and drawing them together from said target location.

4. A method for acquiring access to the central venous system of a patient near an occlusion, comprising the steps of:
   identifying an exit point target site on the exterior skin of a patient near an occlusion;
   introducing a needle wire having a sharp end into a blood vessel at a location remote from said occlusion;
   advancing the needle wire through the vascalature until its sharp end is adjacent the occlusion;
   aiming the sharp end of the needle wire toward the exit point target; and
   advancing the needle wire through the occlusion and through the blood vessel until it becomes exteriorized at the exit point target to establish a tissue track from the blood vessel to the exterior of the patient.

5. The method of claim 4, further comprising introducing a guide catheter with a lumen into the patient at the location remote from the patient and advancing the guide catheter to the occlusion.

6. The method of claim 5, comprising advancing a dilation stylet through the guide catheter to the occlusion, the dilation stylet having a lumen for receiving the needle wire.

7. The method of claim 6, further comprising pulling the dilation stylet out of the body through the exit point to enlarge the tissue track created by the needle wire.

8. The method of claim 6, wherein the step of aiming the sharp end of the needle wire comprises rotating the dilation stylet.

9. A method for acquiring access to the central venous system of a patient near an occlusion, comprising the steps of:
  identifying an exit point target site on the exterior skin of a patient near an occlusion;
  introducing a guide catheter having a first lumen into a blood vessel at a location remote from the exit point target site and advancing the guide catheter to the occlusion;
  advancing a dilation stylet having a second lumen through the guide catheter lumen to the occlusion;
  advancing a needle wire with a sharpened end through the dilation stylet lumen so that the sharpened end is adjacent the occlusion;
  aiming the sharp end of the needle wire toward the exit point target; and
  advancing the needle wire through the occlusion and through the blood vessel until it becomes exteriorized at the exit point target to establish a tissue track from the blood vessel to the exterior of the patient.

10. The method of claim 9, wherein the remote site comprises a femoral vein in a groin of the patient.

11. The method of claim 9, further comprising placing an introducer sheath in the tissue track.

12. The method of claim 9, further comprising pulling the dilation stylet out of the body through the exit point to enlarge the tissue track created by the needle wire.

13. The method of claim 12, further comprising introducing a canalization wire into the dilation stylet.

* * * * *